United States Patent [19]

Cavaterra et al.

[11] 3,939,208
[45] Feb. 17, 1976

[54] PROCESS FOR PREPARING METHACROLEIN FROM ISOBUTENE AND OXYGEN

[75] Inventors: Enrico Cavaterra, Saronno; Donato Petrera, Arenzano; Francesco Pignataro; Gabriele Colucci, both of Milan, all of Italy

[73] Assignee: Montedison S.p.A., Milan, Italy

[22] Filed: July 23, 1974

[21] Appl. No.: 491,062

[30] Foreign Application Priority Data

July 24, 1973 Italy .................................. 26969/73

[52] U.S. Cl. ............................. 260/604 R; 252/456
[51] Int. Cl.² ......................................... C07C 45/04
[58] Field of Search .................. 260/604 R; 252/456

[56] References Cited
FOREIGN PATENTS OR APPLICATIONS
693,086   8/1965   Italy .............................. 260/604 R Primary Examiner—James O. Thomas, Jr.
Assistant Examiner—R. H. Liles

[57] ABSTRACT

Methacrolein is prepared by the gaseous phase reaction of isobutene and oxygen, in the presence of new solid catalysts consisting of the elements tellurium, cerium, molybdenum, of one or more of the elements lithium, sodium potassium, rubidium, cesium and, in addition, of oxygen.

2 Claims, No Drawings

PROCESS FOR PREPARING METHACROLEIN FROM ISOBUTENE AND OXYGEN

THE PRIOR ART

It is known in the art to prepare unsaturated alpha-beta aldehydes from olefins and oxygen in the presence of different catalytic systems. In particular various catalytic systems have been disclosed for use in preparing methacrolein from isobutene and oxygen.

Among the catalytic systems previously proposed for use in preparing methacrolein from isobutene and oxygen are those disclosed in Italian Pat. No. 693,086, consisting of tellurium, molybdenum, cerium and oxygen having the structure of a polyether compound and comprising, optionally, besides the elements mentioned, vanadium.

A review of the relevant patent literature shows that the yields of methacrolein obtained with the prior art catalytic systems is, in general, lower than the yields obtainable in the preparation of acrolein.

Specific processes are known for obtaining methacrolein by the reaction of isobutene and oxygen in the presence of catalysts particularly selected for the purpose. However, even those processes are not entirely satisfactory in practice for the reason that the conversion of isobutene to methacrolein does not exceed, on the average, 60%, and the reaction product is accompanied by considerable quantities of by-products such as: acetaldehyde, acrolein, acetone, acetic acid, acrylic acid, and in consequence the purification of the reaction product for recovery of the methacrolein therefrom is burdensome and costly.

There is a need in the art for a process for obtaining high yields of methacrolein from isobutene and oxygen, not only to insure a low consumption of raw materials but, also, to reduce the amount of difficulty separable by-products formed.

THE PRESENT INVENTION

An object of this invention is to provide a process for obtaining high yields of methacrolein by reacting isobutene and oxygen in the presence of specifically new catalytic systems which are optimum for achieving that object.

That and other objects are accomplished by the process of this invention, in accordance with which excellent yields of methacrolein are obtained and the formation of difficultly separable by-products is inhibited, by reacting isobutene and oxygen in the gaseous phase in the presence of a catalyst consisting of the elements tellurium, and cerium, molybdenum, of at least one of the elements lithium, sodium, potassium, rubidium, and cesium and, in addition, oxygen, in relative amounts such that the atomic ratios of the elements correspond to the formula:

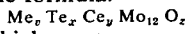

in which:
Me is one or more of the elements Li, Na, K, Rb, Cs;
$v$ is a value from 0.3 to 18;
$x$ is a value from 0.3 to 24;
$y$ is a value from 0.3 to 21;
and $z$ varies widely, corresponding to the quantity of oxygen bound to the other elements (expressed as oxides) in the oxidation states in which they exist in the catalyst defined by the empirical formula given.

For instance, if all of the elements are considered as oxides in their state of maximum valency, $z$ will be comprised between 37.65 and 159. However, while it is conventional in this art to consider the elements specified in the formula as present in the form of oxides in their maximum state of valency, in calculating the value of $z$, that does not mean that all, or even any, of the elements making up the catalyst exist therein as oxides or as oxides in their maximum valency state, in practice.

The present catalysts do consist of the elements tellurium, cerium and molybdenum, and of at least one of the elements Li, Na, K, Rb, and Cs, and in addition, of oxygen, $v$, $x$, and $y$ have the values stated, and the value of $z$ can vary within wide limits depending on the amount of oxygen which is bound to the other elements in the actual oxidation states in which the other elements exist.

The reaction of isobutene and oxygen, which may be mixed with inert diluents such as nitrogen, steam, or the like, in contact with the present catalysts, is usually carried out at a temperature of from 350°C to 500°C, for a contact time of from 0.1 to 10 seconds.

The catalysts used in the process of this invention are highly active even when used without a carrier. In practice, it is preferable to use the catalysts in combination with a carrier or support which may be any suitable material such as, for example, silica, alumina, silicon carbide (carborundum), silica-alumina, phosphates, silicates, borates, and carbonates, provided the carrier is stable under the reaction conditions to which the catalyst will be exposed.

The quantity of the active catalytic composition with respect to the weight of the carrier can vary over a wide range, depending on the characteristics of the carrier and the method of preparing the carried or supported catalyst.

The catalyst can be used in the form of a fixed or fluidized bed. In the latter case, which, as is known in general, has advantages as far as concerns thermal control of the reaction, the nature or character of the carrier and the method used for obtaining a microspheroidal catalyst having a suitable granulometric distribution are of particular importance.

Various techniques may be used for obtaining a microspheroidal catalyst. For example, such a catalyst can be obtained by spray-drying a solution or suspension of the carrier and components of the catalytically active composition, or by impregnating a preformed microspheroidal carrier with a solution of the catalytically active composition.

The catalyst can be prepared by methods which are known in general. More particularly, suitable procedures for preparing a supported catalyst according to the invention for use in the form of microspheroidal particles in a reactor comprising a catalytic fluidized bed are described in Italian Pat. Nos. 751,285 and 789,588.

As starting compounds for the preparation of the catalytic compositions of this invention there can be used the following compounds of alkaline metals: nitrates, oxides, hydroxides, carbonates, bicarbonates, nitrites, molybdates, and salts of oxyacids or of mono- or poly- carboxylic organic acids such as formates, oxalates, citrates and tartrates.

Depending on the method used for preparing the catalyst, the starting molybdenum compounds can be selected from among the ammonium molybdates, alkaline metal molybdates and molybidic anhydride.

The starting cerium compounds can be the nitrate or molybdoceric acid.

Tellurium can be introduced in the form of the oxide, telluric acid, or tellurium powder.

The catalysts can be prepared by known procedures, for instance those disclosed in the Italian Pat. Nos. 693,086 and 789,588.

Whatever method is used to prepare the catalytic composition, it is subjected to a final activation which consists in heating it in the presence of air at a temperature of from 350°C to 750°C, preferably from 450°C to 650°C.

Illustrative methods for preparing the catalytic composition are as follows:

1. An aqueous solution of the ammonium salt of cerimolybdic acid is mixed with a nitric solution of $TeO_2$ and the nitrate of the selected alkaline metal and with a commercial silica aerogel, and after evaporation of the solvent, the catalyst is extruded, dried and activated by heating, preferably at a temperature comprised between 450°C and 650°C.

2. A nitric solution of telluric acid and cerium and alkaline metal nitrates is mixed with a silica gel and an aqueous solution of ammonium paramolybdate is added to the mixture, which is spray-dried to obtain the catalyst in the form of particles which are activated by heating thereof, preferably at a temperature comprised between 450°C and 650°C.

3. An aqueous solution of ammonium paramolybdate is added to a nitric solution of telluric acid and cerium and alkaline metal nitrates, a silica carrier which may be microspheroidal is impregnated with the resulting solution which has a volume equal to the volume of the carrier, the product thus obtained in dried for 12 hours at 110°C – 120°C, and is thereafter activated by heating, preferably at a temperature comprised between 450°C and 650°C.

4. Metallic tellurium powder is added to an aqueous solution of ammonium paramolybdate under vigorous stirring, and then slowly, while hot, $H_2O_2$. Further $H_2O_2$ is then added in the cold state and then $HNO_3$ and the cerium nitrates and alkaline metal nitrates. The resulting solution, suitably diluted with water, is then used for impregnating a commercial silica according to the procedures previously indicated. The product is then dried and activated.

5. Ammonium paramolybdate is dissolved in an aqueous solution of $H_2O_2$ to thereby obtain an aqueous solution of ammonium permolybdate. Separately another solution, acidified by $HNO_3$, is prepared by dissolving telluric acid, $H_2TeO_4 \cdot 2H_2O$, alkaline metal nitrate and cerium nitrate. The solution of permolybdate is then slowly poured into the solution containing the tellurium, cerium and alkaline metal nitrates. The resulting solution, suitably diluted, is used for impregnating a commercial silica. The product is then dried and activated.

Using the catalysts of this invention, high yields of methacrolein are obtained with a very high conversion of the isobutene, up to 100%. These results must be ascribed to the fact that these new catalysts promote an oxidation process with a regular course and easily controllable as regards the reaction temperature and the contact times.

In the oxidation process of the isobutene to methacrolein according to this invention, air is preferably used, as an oxygen source.

As a diluent may also be used water vapour (steam), but this, from the point of view of the results of the reaction, does not offer the advantages claimed for some of the known processes of the prior art.

The reactants may be fed on the catalyst, already pre-heated at a temperature close to the reaction temperature or to room temperature, in which latter case said reactants will heat up rapidly in contact with the catalytic bed, whether it is a fixed or fluidized catalytic bed.

The reactants may be fed to the catalyst already either completely or partially pre-mixed or separately; the feeding of the separate reactants or partially pre-mixed reactants may in general be more conveniently applied to a fluidized bed reactor.

It is also possible to feed all the air and part of the olefin into the lower part of the reactor and to then feed the remaining quantity of olefin in at one or more higher points inside the catalytic bed.

When the reaction is conducted with the technique of the fixed catalytic bed, this latter may be prepared, as known, by placing the catalyst inside the pipes of a tube bundle reactor and by removing the reaction heat by means of suitable cooling fluids circulating externally of the pipes, and for instance, more commonly, by means of mixtures of molten salts. It is also possible to operate in a reactor consisting of several adiabatic reaction stages alternated with cooling zones for the reacting mixture.

The reaction can be conducted at a temperature comprised between 350° and 500°C, but which is preferably comprised between 380° and 480°C.

The contact time, expressed in seconds as the ratio between the volume of the catalytic bed and the volumes per second of the fed gaseous reactant mixture, measured under the average temperature and pressure conditions existing in the catalytic bed, may vary in relation to the temperature and to the nature of the catalyst, the nature of the catalytic bed, either fixed or fluidized, and in relation to the granulometric size of the catalyst; in general said contact time may be comprised between 0.1 and 10 seconds. However, a preferred time range, corresponding to the most common practical conditions of use, is comprised between 0.2 and 6 seconds.

The total pressure under which the reaction is conducted is not particularly significant and thus may vary within wide limits, although it is partly suggested by economical considerations. In general, pressures near to atmospheric pressure and more particularly slightly above atmospheric pressure are used.

In the process of this invention there are used gaseous mixtures of reactants wherein the molar ratio $O_2$/isobutene is comprised between 1.0 and 10, preferably between 1.5 and 5.

The following examples are given to illustrate the invention and are not intended to be limiting.

EXAMPLE 1

A. Preparation of the catalyst

In 20 ml of distilled $H_2O$ and 14 ml of a 30% $H_2O_2$ (120 vol.) were dissolved 38.40 g of $(NH_4)_6 Mo_7O_{24} \cdot 4H_2O$ (ammonium paramolybdate.)

Separately, another solution was prepared by dissolving 16.50 g of $H_2TeO_4 \cdot 2H_2O$; 3.03 g of $KNO_3$ and 39.10 g of $Ce(NO_3)_3 \cdot 6H_2O$ in 80 ml of $H_2O$ and 20.00 g $HNO_3$ at a 65% by weight concentration. The solution containing the molybdenum was then slowly poured into the solution containing the tellurium, the potassium and the cerium.

The resulting solution was then diluted with $H_2O$ until a volume equal to the volume of the pores of the silica carrier was attained, and thereafter a quantity of commercial granular silica corresponding to 175 g of dry silica was impregnated with the diluted solution.

The product thus obtained was thereupon dried for 12 hours at 110° – 120°C and then activated in air at 500°C. The catalyst thus obtained contained about 75% by weight of $SiO_2$. In the chemical combination of the catalyst the elements: Te, K, Ce and Mo are present in atomic ratios represented by the formula:

$Te_4K_{1.65}Ce_5Mo_{12}$.

B. Process of oxidation

The oxidation reaction was carried out in a reactor loaded with the above mentioned catalyst in the form of a fixed bed. The reaction conditions and the results are reported in Table I (Ex. 1). Therein, for selectivity is meant the ratio:

$$\frac{\text{grams of obtained C of the desired product}}{\text{grams of C of the reacted isobutene}} \times 100$$

EXAMPLES 2 – 5

These examples were carried out with the same equipment as used in Example 1.

The different catalysts used were characterized by different quantities of K as indicated in Table I (Exs. 2 – 5).

The reaction conditions and results are also reported in Table I.

EXAMPLES 6 – 10

These examples were carried out with the same equipment as used in Example 1.

The different catalysts were characterized by the different quantities and quality of alkaline metals, as indicated in Table I (Exs. 6 – 10), which Table also shows the reaction conditions and the results.

EXAMPLES 11 – 18

The same equipment as was used in Example 1 was used.

The different catalysts, all of the empirical formula $K_{1.65}Te_4Ce_5Mo_{12}$, are characterized by different activation temperatures which are indicated in Table I (Exs. 11 – 18), as are the reaction conditions and the results.

EXAMPLES 19 – 20

These examples were carried out with the same equipment as that described in Example 1. The different catalysts were characterized by different ratios of the elements tellurium and cerium with respect to the molybdenum, as indicated in Table I.

Table I also shows the reaction conditions and the results.

EXAMPLE 21

The same catalyst as that of Example 1, tested for a prolonged period of time under the conditions indicated in Example 1, and, at the limit of 85 hours, gave the following results:

| | |
|---|---|
| Conversion of isobutene | 92.2% |
| Selectivity: methacrolein | 77.5% |
| Selectivity: $CO + CO_2$ | 22.5% |
| Yield in methacrolein | 71.5% |

TABLE I

| Atomic ratios Active elements of Catalyst | Activation temperature of Catalyst °C | Reaction Temperature °C | Air/$iC_4$— v/v | Contact time in seconds | Conversion $iC_4$— | Selectivity MAH | Selectivity CO | Selectivity $CO_2$ | Yield MAH | |
|---|---|---|---|---|---|---|---|---|---|---|
| $K_{1.65}Te_4Ce_5Mo_{12}$ | 500 | 430 | 22 | 0.5 | 98.7 | 76.2 | 8.0 | 15.8 | 75.2 | $iC_4$ = isobutene |
| —$Te_4Ce_5Mo_{12}$ | 500 | 430 | 22 | 0.5 | 100.0 | 59.4 | 14.4 | 26.2 | 59.4 | |
| $K_{1.65}Te_4Ce_5Mo_{12}$ | 500 | 430 | 22 | 0.5 | 98.7 | 76.2 | 8.0 | 15.8 | 75.2 | MAH = methacrolein |
| $K_{3.30}Te_4Ce_5Mo_{12}$ | 500 | 430 | 22 | 0.5 | 93.6 | 78.5 | 6.0 | 15.5 | 73.5 | |
| $K_{4.95}Te_4Ce_5Mo_{12}$ | 500 | 425 | 22 | 1.0 | 94.5 | 75.5 | 7.0 | 16.5 | 71.5 | |
| $K_{1.65}Te_4Ce_5Mo_{12}$ | 500 | 430 | 22 | 0.5 | 98.7 | 76.2 | 8.0 | 15.8 | 75.2 | |
| $Li_{9.88}Te_4Ce_5Mo_{12}$ | 500 | 425 | 22 | 1.0 | 91.9 | 72.9 | 6.6 | 20.5 | 67.1 | |
| $Na_7Te_4Ce_5Mo_{12}$ | 500 | 455 | 23 | 0.5 | 90.8 | 73.9 | 5.2 | 20.9 | 67.0 | |
| $Rb_{3.5}Te_4Ce_5Mo_{12}$ | 500 | 470 | 24 | 0.5 | 93.5 | 67.4 | 11.3 | 21.3 | 63.0 | |
| $Cs_{2.5}Te_4Ce_5Mo_{12}$ | 500 | 450 | 22 | 0.5 | 97.6 | 73.8 | 9.1 | 17.1 | 72.0 | |
| $K_{1.65}Te_4Ce_5Mo_{12}$ | 500 | 430 | 22 | 0.5 | 98.7 | 76.2 | 8.0 | 15.8 | 75.2 | |
| " | 520 | 420 | 23 | 0.5 | 97.7 | 81.6 | 7.0 | 11.4 | 79.2 | |
| " | 540 | 430 | 23 | 0.5 | 96.8 | 78.3 | 6.5 | 15.2 | 75.8 | |
| " | 560 | 430 | 24 | 0.5 | 98.8 | 80.6 | 7.1 | 12.3 | 79.6 | |
| " | 580 | 430 | 22 | 0.5 | 94.1 | 80.7 | 7.5 | 11.8 | 75.8 | |
| " | 600 | 440 | 22 | 0.5 | 93.9 | 79.5 | 8.3 | 12.2 | 74.7 | |
| " | 650 | 435 | 22 | 2.5 | 99.1 | 67.2 | 13.8 | 18.4 | 65.9 | |
| " | 700 | 430 | 23 | 2.4 | 98.4 | 73.2 | 11.5 | 15.3 | 72.0 | |
| $K_5Te_2Ce_5Mo12$ | 500 | 446 | 22 | 0.6 | 88.2 | 79.0 | 6.0 | 15.0 | 69.6 | |
| | 500 | 433 | 21 | 0.5 | 89.0 | 77.4 | 4.7 | 18.0 | 69.0 | |

We claim:

1. A process for obtaining methacrolein from isobutene by reaction thereof in a gaseous phase with oxygen or oxygen containing gaseous mixtures, at a temperature comprised between 350° and 500°C, characterized in that in said process there is used a catalytic system consisting of a chemical combination of the elements: tellurium, cerium, molybdenum, at least one element selected from the group consisting of Na, K, Li, Rb and Cs, and, in addition, of oxygen, the different elements being present in the catalytic system in atomic ratios represented by the following formula: $Me_vTe_xCe_yMo_{1-2}O_z$, wherein Me is Na, K, Li, Rb, Cs or mixtures thereof, $v = 0.3 - 18$, $x = 0.3 - 24$, $y = 0.3 - 21$ and $z$ corresponds to the quantity of oxygen bound to the other elements and corresponding to their state of oxidation in the catalyst.

2. The process according to claim 1, in which the catalytic combination is supported on a silica carrier.

* * * * *

UNITED STATES PATENT OFFICE
CERTIFICATE OF CORRECTION

Patent No. 3,939,208            Dated February 17, 1976

Inventor(s) Enrico Cavaterra et al.

It is certified that error appears in the above-identified patent and that said Letters Patent are hereby corrected as shown below:

Col. 3, line 35, "in" before "dried" should be – – – is – – –.

Cols. 5 and 6, Table 1 the first col. of the Table, shown at page 13 of the specification and headed "Ex. No.", should be part of the printed Table.

Cols. 5 and 6, Table 1, second col.

Under the heading "Atomic ratios active elements of Catalyst", the last item of said column as shown at page 13 of the specification, – – – $K_{3.33}Te_4Ce_7Mo_{12}$ – – – is omitted and should appear.

Signed and Sealed this

First Day of August 1978

[SEAL]

Attest:

RUTH C. MASON           DONALD W. BANNER
Attesting Officer        Commissioner of Patents and Trademarks